(12) United States Patent
Bilimoria

(10) Patent No.: US 6,200,561 B1
(45) Date of Patent: Mar. 13, 2001

(54) USE OF VIRAL PROTEINS FOR CONTROLLING THE COTTON BOLL WEEVIL AND OTHER INSECT PESTS

(76) Inventor: Shän L. Bilimoria, 5319 85th St., Lubbock, TX (US) 79424

( * ) Notice: Subject to any disclaimer, the term of this patent is extended or adjusted under 35 U.S.C. 154(b) by 0 days.

(21) Appl. No.: 09/209,599

(22) Filed: Dec. 11, 1998

(51) Int. Cl.[7] .............................. A01N 63/00; A61K 35/76
(52) U.S. Cl. ...................... 424/93.6; 424/204.1; 424/115; 43/132.1; 47/58.1
(58) Field of Search ................................ 514/2; 424/93.6, 424/204.1, 115; 47/58.1; 43/132.1

(56) References Cited

U.S. PATENT DOCUMENTS

| | | |
|---|---|---|
| 4,745,051 | 5/1988 | Smith et al. . |
| 5,180,581 | 1/1993 | Miller et al. . |
| 5,306,628 | 4/1994 | Sivasubramanian et al. . |
| 5,352,451 | 10/1994 | Miller et al. . |
| 5,558,862 | 9/1996 | Corbin et al. . |
| 5,662,897 | 9/1997 | Miller et al. . |

FOREIGN PATENT DOCUMENTS

WO 92/21753    6/1992  (WO) .

OTHER PUBLICATIONS

Cerutti et al. Archives of Virology 63 (3/4): 297–703, 1980.*
Jensen et al. J. Invertebrate Pathology 19:276–278, 1972.*
McLaughlin, et al Infection of the Boll Weevil by Chilo Iridescent Virus McLauglin, Scott and Bell Jun. 18, 1971.

Purcell, et al Biochemic & Biophysical Research Communication vol. 196, No. 3, 1993 Cholesterol Oxidase: A Potent Insecticidal Protein Active Against.

Steve O'Neil Tech Researchers make shrides in developing weevil –resistant cotton Lubbock Avalanche Apr. 16, 1995.

Cerutti, et al Inhibition of Macromolecular Synthesis in Cells Infected Archives of Virology 63, 297–303 (1980).

Charles Melton Tech–engineered virus May Limit Weevils The University Dailey Nov. 18, 1995.

Fondy commentator 1 Spring 1996 Just Call Them "The Bollweevil Devils".

Proceedings of the Southwestern and Rock Mountian Division American Asso. for the Advancement of Science 72nd Annual Meeting vol. 36, No. 1 Jun. 2–6, 1996.

* cited by examiner

Primary Examiner—Mary E. Mosher
(74) Attorney, Agent, or Firm—Henry Croskell

(57) ABSTRACT

A protein extract from Chilo iridescent virus or the whole virus controls insects, particularly the cotton boll weevil and the cotton aphid, respectively. These compositions/agents may be used to directly control insects or genes for active proteins may be cloned into vectors for transformation of plants or plant colonizing microorganism, thereby providing a method for controlling insect infestation.

12 Claims, 6 Drawing Sheets

FIGURE 1. Effect of viral protein extract on neonate boll weevil larvae.
Approximately 100 eggs were placed in Petri dishes containing boll weevil agar medium and allowed to hatch. Neonate larvae were sprayed with 500 μl viral protein extract (5 μg protein/ml; ■), or with buffer solution (●), or were not treated (◆).

FIGURE 2. **Effect of *Chilo* iridescent virus on cotton aphid populations.** Fifteen aphids were placed on leaves that had been treated as follows: i) brushed with 10 mg/ml virus in casein buffer, ii) brushed with casein buffer only, or iii) untreated. After three days, the leaves were examined for aphid mortality. Results are presented as percent decrease in populations with respect to untreated leaves. Each experiment was performed in triplicate.

A

μg/ml    μg/ml
Δ M 50 25 10    Δ M 10 25 50

B

M P T

CF CELLS    AG CELLS    AG CELLS

FIGURE 3. Inhibition of protein synthesis by protein extract from *Chilo* iridescent virus. A) AG (boll weevil) and CF (spruce budworm) cells were treated with viral extract at the indicated concentrations. Controls consisted of mock treatment (M), which contained no extract, or treatment with heated extract, Δ (50 μg/ml extract heated at 65 °C, 30 min). Cells were incubated at 28 °C for 3 hr, starved for 2 hr, and pulsed with 80 μCi/ml $^{35}$S-methionine for 1 hr. Cellular protein was then fractionated by SDS-PAGE on a 10% gel, which was then dried and exposed to X-ray film. B) AG cells exposed to 50 μg/ml proteinase K-treated extract (P; 50 μg/ml *Proteinase K*, 37 °C, 2 hr) showed the same levels of protein synthesis as mock-treated cells (M). Both sets of cells synthesized significantly more protein than cells treated with 50 μg/ml of the toxin extract (T). Methodology was the same as above except that the incubation period was 1 hr.

TOXIN MOCK

CF

AG

FIGURE 4. Protein extract from *Chilo* iridescent virus induces blebs characteristic of programmed cell death (apoptosis) in boll weevil and spruce budworm cells. Cells were treated with toxin at 2 µg/ml or mock- treated and incubated at 28 °C for 24 hr. CF, spruce budworm (CF124T) cells; AG, boll weevil (BRL-AG-3A) cells.

TABLE 1. Dose response analysis for induction of blebbing by viral protein extract.

| TOXIN (μg/ml) | PERCENT CELL BLEBBING | | | |
|---|---|---|---|---|
| | BOLL WEEVIL CELLS | | BUDWORM CELLS | |
| | REPLICATE 1 | REPLICATE 2 | REPLICATE 1 | REPLICATE 2 |
| 20 | ++++ | ++++ | ++++ | ++++ |
| 4 | ++++ | ++++ | ++++ | ++++ |
| 0.8 | ++++ | ++++ | ++++ | ++++ |
| 0.16 | ++++ | ++++ | ++++ | ++++ |
| 0.032 | ++± | ++++ | ++++ | ++++ |
| 0.006 | - | + | +++± | ++++ |
| 0.001 | - | ± | + | + |

Boll weevil (AG) and budworm (CF) cells were treated in duplicate with serial 5-fold dilutions of viral protein extract. Cultures were incubated for 48 hours at 28 °C and then scored. Each "+" symbol approximates blebbing in 25 percent of the cell population. The 50 percent end-point titer for the extract is 32 ng/ml for AG cells and 6 ng/ml for CF cells.

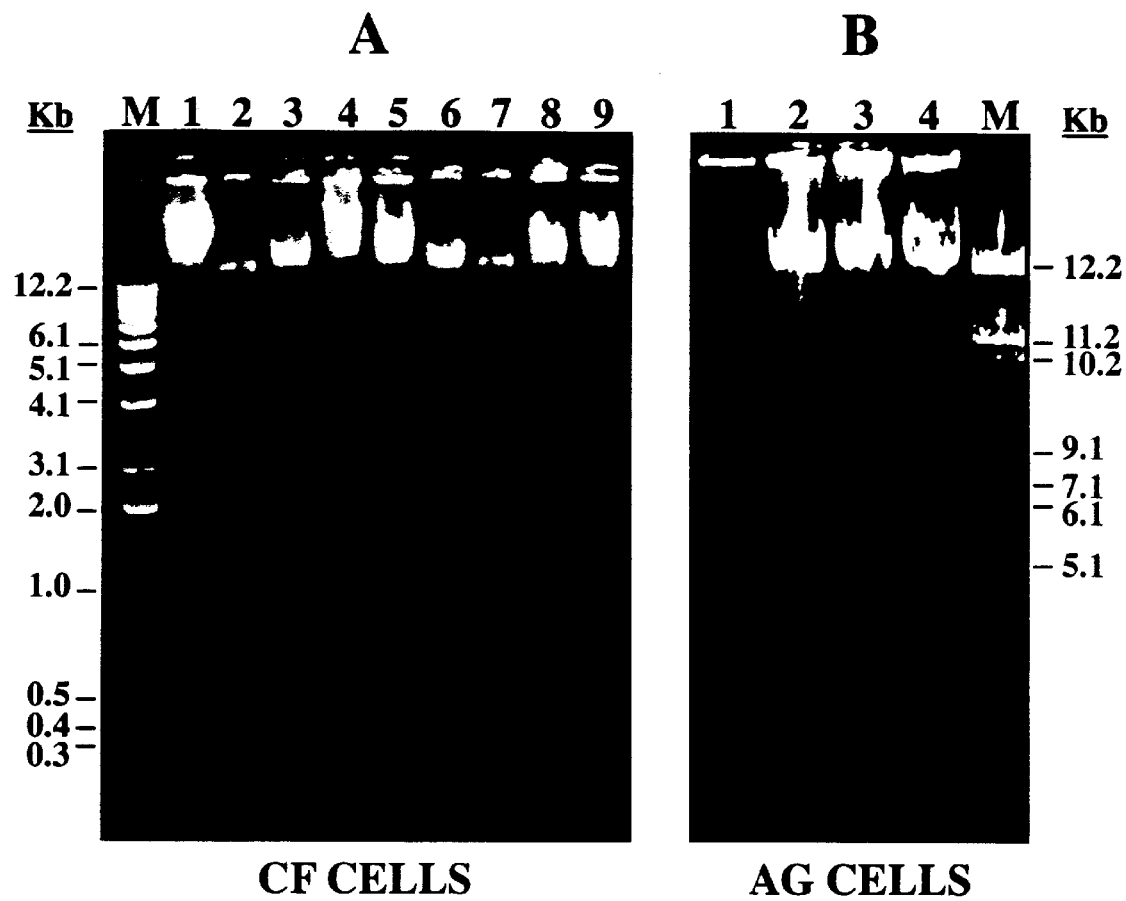

FIGURE 5. Induction of DNA fragmentation by viral protein extract. Spruce budworm and boll weevil cells treated with protein extract from *Chilo* iridescent virus undergo DNA fragmentation or smearing, respectively. These responses are characteristic of programmed cell death (apoptosis). A. Budworm cells (CF) were treated as follows. Positive controls, actinomycin D: (1) 1 µg/ml; (2) 4 µg/ml. Negative control: (3) mock-infection with culture medium only. Infection with larval-derived virus: (4) 10 µg/ml; (5) 5 µg/ml. Treatment with viral protein extract: (6) 5 µg/ml; (7) 2.5 µg/ml. Additional negative controls: (8) mock treated with buffer only; (9) untreated. Molecular weight standards are to the left. B. Boll weevil cells (AG) were treated as follows. Positive control: (1) actinomycin D, 1 µg/ml. Treatment with viral protein extract: (2) 4 µg/ml; (3) 7.5 µg/ml. Negative control: (4) Mock treatment with buffer only. Molecular weight standards (M) are to the right.

USE OF VIRAL PROTEINS FOR CONTROLLING THE COTTON BOLL WEEVIL AND OTHER INSECT PESTS

FIELD OF THE INVENTION

This invention relates to a method of controlling insects, including particularly weevils, cotton boll weevils etc. by use of a viral protein extract which may be applied directly to the boll weevil or larva or cotton plants. In another aspect, the invention relates to an isolated gene from the viral toxin which can be transferred to plant crops such as cotton so that toxin will be produced in such engineered plants.

BACKGROUND OF THE INVENTION

The use of natural products, including proteins, is a well-known method of controlling many insect pests. Endotoxins of *Bacillus thruringiensis* (*B.t.*) are used to control both lepidopteran and coleopteran insect pests. Genes producing the *B.t.* toxin have been introduced and expressed in several plants, including cotton, tomato, and tobacco, and have also been expressed by various microorganisms. However, there are several economically important insect pests that are not susceptible to *B.t.*endotoxins, and this group includes the cotton boll weevil. Researchers at the Monsanto Co. have identified a bacterial enzyme (cholesterol oxidase) that induces mortality and stunting in boll weevil larvae and in several lepidopteran species. These workers have isolated the gene for this enzyme and expressed it in plant-colonizing bacteria and in cotton tissue culture. Experience with *B.t.* toxins suggests that development of resistance will be a problem with use of protein toxins for insect control, and a number of approaches have been recommended to minimize this. These include the use of refugia, dosage control, and use of multiple toxins, etc. An important strategy against the development of resistance will be the identification of alternate toxins that have a different mode of action. This approach will allow use of lower doses for all toxins and will minimize the probability of mutations that result in resistance to two or more toxins.

There are, however, several economically important insect pests that are not susceptible to *B.t.* endotoxins. One such important pest is the cotton boll weevil. There is also a need for additional proteins which control insects for which *B.t.* or other toxins provides control in order to manage any development of resistance in the population.

Interest in the biological control of insect pests has arisen as a result of disadvantages of conventional chemical pesticides. Chemical pesticides generally affect beneficial as well as nonbeneficial species. Insect pests tend to acquire resistance to such chemicals so that new insect pest populations can rapidly develop that are resistant to these pesticides. Furthermore, chemical residues pose environmental hazards and possible health concerns. Biological control presents an alternative means of pest control which can reduce dependence on chemical pesticides.

The primary strategies for biological control include the deployment of naturally-occurring organisms which are pathogenic to insects (entomopathogens) and the development of crops that are more resistant to insect pests. Approaches include the identification and characterization of insect genes or gene products which may serve as suitable targets for insect control agents, the identification and exploitation of previously unused microorganisms (including the modification of naturally-occurring nonpathogenic microorganisms to render them pathogenic to insects), the modification and refinement of currently used entomopathogens, and the development of genetically engineered crops which display greater resistance to insect pests.

In 1972 McLaughlin et al. published their work on the effect of CIV on the cotton boll weevil. They showed that infection with whole virus arrested metamorphosis and death. Researchers in France showed that soluble extracts from CIV inhibited host protein synthesis and gene expression in cell cultures from mosquitoes and some caterpillar species (Cerutti and Devauchelle, 1980). However, no group has previously shown that a protein fraction from CIV kills boll weevil larvae, nor has any group shown whole virus or viral protein preparations causing inhibition of protein synthesis in boll weevil cell lines or induction of programmed cell death (apoptosis) in any cell line.

The cotton boll weevil will have an economic impact exceeding $500 million per year in Texas alone. More than 9,200 jobs will be lost and at least 60 cotton gins will close if no new technology is developed. Chemical control of the weevil is not working well because of resistance problems and adverse effects on beneficial insects. In addition, there are difficulties in discovering new chemistry and problems with insecticide contamination of ground reserves. Therefore, the development of alternative, biological (especially microbial) control systems is critical. Because larvae develop inside the cotton boll and cannot be sprayed externally, the best control strategy will be to engineer transgenic cotton that produces insecticidal proteins.

Our laboratory has shown that Chilo iridescent virus (CIV) induces metamorphic deformity in boll weevil larvae, and kills them. We have shown that CIV replicates efficiently in this host. A protein extract from the virus induces mortality in neonate larvae. The Extract also inhibits host protein synthesis and minduces programmed cell death or apoptosis as evidenced by cell blebbing and DNA fragmentation. Heating at 60 degrees C. for 30 minute or treatment with protease destroys these activities.

Prior art has shown that Chilo iridescent virus (CIV) induces mortality and metamorphic deformity in the cotton boll weevil. Prior art also shows that CIV protein extracts inhibited host gene expression in lepidopteran and dipteran cells. However, the use of CIV protein extracts in the control of in sect infestation have not been demonstrated nor has it been demonstrated that CIV protein extract induces programmed cell death or apoptosis in any cell line or organism.

What is needed is a biological pesticide which reduces the adverse effects of chemical pesticide. A biological pesticide is preferred because it creates less of an environmental hazard than a chemical pesticide. A pesticide that causes insect death more rapidly is additionally needed. What is also needed to the identification and isolation of a gene that codes for a protein which will control insect development. Such a gene or its protein product could then be incorporated into various organisms for the improved biological control of insect pests.

SUMMARY OF THE INVENTION

It has been discovered that a protein extract from purified Chilo iridescent virus (CIV) particles will control infestations by boll weevils, and whole virus particles will control aphid populations.

It has been discovered that proteins or extracts of proteins that are insecticidal proteins provide composition and methods for using certain viral inhibitors to protect plants otherwise susceptible to insect infestation by one or more of Mexican bean beetle, red flower beetle, confused flower beetle, boll weevil, Colorado potato beetle, 3-line potato beetle, rice weevil, maze weevil, granularly weevil, Egyptian alfalfa weevil, bean weevil, yellow mill worm weevil, asparagus beetle and a variety of other insects including other beetles and weevils.

We have shown that a protein fraction from purified Chilo iridescent virus particles causes mortality in freshly hatched larvae of the cotton boll weevil. This toxin preparation also inhibits wholesale protein synthesis, and induces programmed cell death (apoptosis) in cell cultures of the cotton boll weevil, *Anthonomus grandis*. Knowledge of the viral toxin will allow isolation of the gene responsible for the toxin. The gene would then be transferred to crop plants (such as cotton) so that toxin will be produced in such engineered plants. Pest insects will be arrested in their development or die upon contact with toxin producing plant tissues. The toxin is the only way viral protein component is known to kill boll weevil larvae. It is also the only viral toxin that inhibits host protein synthesis and induces programmed cell death in boll weevil cells. The toxin will be used to engineer pest resistance for all plants. Its unique mechanism of action will also reduce development of resistance to other toxins.

The protein extract is lethal to boll weevil larvae and will interrupt protein synthesis in boll weevil cells and induce programmed cell death or apoptosis in them. This mechanism of action is distinct from that of cholesterol oxidase, which alters the insect gut environment by inducing changes in lipids surrounding essential enzymes, such as alkaline phosphatase. CIV particles will induce mortality in aphid populations. The protein extract or virus may be applied directly to the plants or introduced in other ways, such as expression in plant-colonizing microorganisms or in crop plants, after isolation of the toxin gene. Tests on the effect of toxin on aphid populations are in progress.

As used herein, the term "controlling insect infestation" means reducing the number of insects which cause reduced yield, through either mortality, retardation of larval development (stunting), or reduced reproductive efficiency.

Present technology utilizes chemical insecticides to control the boll weevil and other insect pests. Microbial insecticides are being developed to address problems of resistance and environmental damage. A number of protein toxins against caterpillars have been identified, and at least one (the *B.t.* toxin) has been used to engineer caterpillar-resistant plants (Meeusen, R. L. and Warran, G. 1989. Ann. Rev.Entomol. 34:373–381). Thus far only one other class of toxin, cholesterol oxidase (Purcell et al., Biochem. Biophys. .Res.Comm. 196: 1406–1413. 1993; Corbin et al., U.S. Pat. Appl. Nos. 475,964; 083,948, 1995), has been identified against the boll weevil. It should be emphasized that our toxin works by a mechanism that is different from that of cholesterol oxidase and is in a different class altogether. For any pest, it is critical to develop several different toxins or genes, each working through a different mechanism, in order to avoid the problem of resistance in the target population. Thus, the toxin we have developed will play a novel and useful role in pest control.

Accordingly, it is an object of the present invention to provide a gene and its gene product that are useful in the control of insect pest.

It is another object of the present invention to provide a recombinant virus that is a more effective pesticide than wild type virus. It is yet another object of the present invention to provide a genetically engineered virus that is an effective pesticide and is also environmentally acceptable. It is yet another object of the present invention to provide a modified biological pesticide that express es a genetically inserted gene.

It is another object of the present invention to provide a novel use of viral proteins and protein extracts for controlling cotton boll weevil and other insects. In yet another object of the invention is the demonstration that a protein fraction from purified Chilo iridescent virus particles causes mortality in freshly hatched larvae of the cotton boll weevil.

It is another object of the present invention to provide a modified biological pesticide that inhibits with viral extract which induces cellular suicide (apoptosis) in boll weevil, bud worm cells and aphids.

Also contemplated is insecticidal compositions, those comprising an agriculturally suitable carrier and genetically modified insect parasite. An insect parasite is an organism which lives or replicates in close association with an insect larva, and has adverse affects on that larvae An insect parasite can be a bacterium, a fungus, a virus or another insect. Such a genetically modified insect parasite comprising toxin gene will be improved as an insect control agent by the insertion and expression of a toxin gene.

Any of the above-noted insecticidal compositions may further comprise ingredients to stimulate insect feeding. The insecticidal compositions of the present invention can be ingested by insect pests after plant application, and those insect pests susceptible to the insect control agent in the insecticidal composition will exhibit reduced feeding and will die.

It is therefore an object of the present invention to provide proteins capable of controlling insects, such as boll weevils and lepidopterans, and genes useful in producing such proteins. It is a further object of the present invention to provide genetic constructs for and methods of inserting such genetic material into microorganisms. It is another object of the present invention to provide transformed microorganisms containing such genetic material.

BRIEF DESCRIPTION OF THE DRAWINGS

FIG. 1 shows the effect of spraying viral protein extract on neonate boll weevil larvae compared to mock treated and untreated larvae.

FIG. 2 shows the effect of virus infection on populations of cotton aphids on cotton leaves.

FIG. 3 shows inhibition of protein synthesis in boll weevil and budworm cells as a result of treatment with viral protein extract.

FIG. 4 shows blebbing typical of apoptosis induced by viral protein extract.

Table 1. shows dose response for blebbing induced by viral protein extract in boll weevil and budworm cells.

FIG. 5 shows DNA fragmentation typical of apoptosis due to viral protein extract.

DETAILED DESCRIPTION OF THE INVENTION

The use of CIV protein extracts for controlling insects is within the scope of this invention. Additionally, it is contemplated herein that the compositions of the inventions will include isolation and expression of the toxin gene in plant-colonizing microbes and in crop plants. Virus purification and extraction Virus production: The procedures for purification of CIV are well known in the art and used for other iridescent viruses. Chilo iridescent virus was reared in the greater wax worm, *Galleria mellonella*. Waxworm larvae were nicked with sharpened forceps that had been dipped in a virus suspension (0.5 µg/ml). Larvae were checked every three days in order to remove dead and pupated insects. All other larvae were frozen at −20 degrees C. two weeks after infestation. Virus was purified from the waxworm larvae by maceration in Tris-NaCl buffer (50 mM Tris-HCl, 150 μM NaCl, ph 7.4) using a Waring blender. The slurry was filtered through cheesecloth into Sorvall GSA centrifuge tubes to remove large particulate material. The supernatant was then transferred into SS-34 centrifuge tubes and centrifuged at 17,000 rpm for 30 minutes at 4 degrees C. After overnight resuspension of the virus pellet in Tris-NaCl buffer, the suspension underwent another round of differential centrifugation in SS-34 tubes. After overnight resuspension of the second pellet, the virus pellet in Tris-NaCl buffer, the suspension underwent another round of differential centrifugation in SS-34 tubes. After overnight resuspension of the second pellet, the virus was layered on top of 10–60 percent sucrose (w/v) gradients and centrifuged for 2 hours at 36,000 rpm at 4 degrees C. Viral layers were harvested, pelleted, resuspended, and run on a second set of sucrose gradients. The resulting virus layers were pelleted, resuspended, and filtered through a series of 0.45 and 0. 22 μm pore-size filters. The concentration of the virus was determined by spectrophotometric analysis. One unit of absorbance at 260 nm (A260) equals 55 μ/ml of virus. Production of viral protein extracts: The preparation of viral protein extracts are well known in the art and used for several viruses, including iridescent viruses. CHAPS extractions: Five milligrams of sucrose gradient-purified virus is pelleted and resuspended in CHAPS extraction buffer (10 μM Tris-HCL, 10 mM CHAPS, and 1M KCl, pH 7.4) in a final volume of 10 μg/ml. The suspension is then incubated at 30 degrees C. for 15 minutes and 5 μl of the suspension is layered on top of 6 ml of 20 percent sucrose in SW-41 centrifuge tubes. The suspension is centrifuged for 2 hours at 36,000 rpm at 4 degrees C. The supernatant above the sucrose is then collected and subjected to four rounds of ultrafiltration using a YM-10 membrane with storage buffer (50 mM Tris-HCl, 150 mM NaCl, ph 7.4) to a final volume of approximately 1 ml. The extract is then filtered through a 0.22 μm filter and stored at −80 degrees C. Membrane Filtration: Virus is resuspended in Borate buffer (0.01 M Borate, pH 7.5) and stirred overnight at 4 degrees C. to facilitate protein release. The suspension is then filtered through a YM-100 membrane, followed by concentration to approximately 1 ml using a YM-10 membrane. The extract is then filtered through a 0.22 im filter and stored at −80 degrees C.

Bioefficacy Essays

Effect of viral protein extract on neonate boll weevil larvae: Boll weevil growth medium containing eggs of the cotton boll weevil, *Anthonomus grandis* (obtained from the GAST laboratory, Starkville, Miss.) were divided into square sections just large enough to fit standard Petri dishes. Each dish contained approximately 100 eggs. Upon hatching of the eggs, the medium surface was sprayed with approximately 500 μl of either a soluble protein extract (5 μg/ml) and the antibiotic gentamicin (50 μg/ml) or identical buffer without viral protein. Eight days after initial treatment, insects were removed from the dishes, observed for mortality, and again sprayed with approximately 500 μof the appropriate treatment. Larvae were observed daily for the next eight days.

FIG. 1 shows that treatment with viral protein extract killed 37 percent of neonate larvae populations, whereas only seven percent of buffer-treated and five percent of untreated larvae were killed. The data show that viral protein extract for Chilo iridescent virus has insecticidal properties. Active extracts contained approximately seven major and eleven minor polypeptides of varying relative abundance.

Effect of Chilo iridescent virus on the cotton aphid, *Aphis gossypii*: Cotton leaves were brushed with 10 μg/ml purified (twice through sucrose gradients) Chilo iridescent virus in Tris NaCl buffer (50 mM Tirs-HCl, 150 mM NaCl, pH 7.4) containing 15 μg/ml casein as a carrier protein and the protease inhibitors Leupeptin (2 μg/ml) and Pepstatin A (1 μg/ml). Mock treatments (consisting of buffer preparation) and untreated leaves served as negative controls. After brushing, 15 aphids were placed in a small area on the underside of cotton leaves. In order to contain the aphids, the bottom portion of a 30-μm plastic Petri dish (with a covered hole for ventilation) was placed over the leaf surface containing aphids, while the top portion was inverted and placed on the opposite side of the leaf. The apparatus was held together with clamps and the leaves were supported on a shelf. After three days incubation, treated and control leaves were removed from the cotton plants and aphid numbers and mortality were determined using a dissecting microscope. Results are shown as percent decrease in live aphid numbers with respect to untreated samples. The assay was performed in triplicate.

FIG. 2 shows that compared to untreated control groups, aphid population growth is reduced by 65 percent when treated with Chilo iridescent virus. Mock treatments with casein reduced population growth by only 30 percent. The results suggest a significant viral effect and indicate that CIV is an effective viral insecticide against aphids.

Inhibition of Protein Synthesis by Viral Protein Extract

Boll weevil (BRL-Ag-3A: AG) and spruce budworm (CF124T; CF) and cells ($6.25\times10^5$ cells/ml) were seeded into 24-well tissue culture trays. After overnight attachment at 28 degrees C., culture medium was removed and cells were washed with unsupplemented medium. Subsequently, the cells were incubated for 3 hours at 28 degrees C. and starved of methionine for two hours in 100 μl ExCell 401 methionilne-eficient medium (JRH Biosciences). Following starvation, the cells were labeled for one hour with 150 μl ExCell 401 methionine-deficient medium containing 80 μCi/ml $^{35}$ S-methionine. Cells were then removed from well matrices using a rubber policeman; samples were centrifuged for 30 seconds and resuspended in SDS-PAGE sample buffer. Samples were then boiled for 5 minutes and analyzed on a 10 percent SDS-polyacrylamide gels. Gels were immersed in protein fixing solution (30 min), submerged in $En^3$Hance (Dupont NEN) for 15 minutes, and precipitated in ice-cold water for 15 minutes. Gels were then dried onto filter paper and exposed to Hyperfilm MP X-ray film (Amersham) at −80 degrees C. before developing.

FIG. 3 shows that host protein synthesis in both boll weevil and spruce budworm lines is drastically reduced with viral protein concentrations of 10 μg/ml. Untreated cells or cells treated with heated viral protein did not inhibit host synthesis and neither did treatment with Proteinase K (Sigma: 50 μg/ml, 37 degrees C., 2 hr). These data indicate that the inhibiting viral factor is a protein. Thus, a polypeptide (or polypeptides) in the viral extract has an inhibitory effect on protein synthesis in boll weevil and spruce budworm cells.

Induction of Programmed Cell Death by Viral Protein Extract

Two major manifestations of virus-induced programmed cell death or apoptosis are the formation of blebs and fragmentation of cellular DNA. We show that protein extracts from purified CIV induce both of these effects in boll weevil and spruce budworm cells.

Bleb formation: Serial ten-fold dilutions of the toxin preparation (in the range 150 μg/ml to 150 pg/ml) were prepared and used for treating cell cultures. An equal volume of cell suspension (BRL-AG-3A cells at $5\times10^5$ cells/ml or CF 124T cells at $7.5\times10^5$ cells/ml) and the appropriate dilution of toxin solutions were mixed, and 15 ml of this preparation was added to each well of a 60-well Terasaki plate. The plates were then placed in a sandwich bag along with a moistened paper towel and incubated at 28 degrees C. The assay was done in duplicate using mock-treated cells (buffer only) as controls. Cells were examined at 24 hours post treatment for cytopathology.

FIG. 4 shows that both boll weevil and spruced budworm cells manifest blebbing. This is characteristic cells undergoing apoptosis. The formation of coronas and blebs are more numerous in the spruce budworm cells, but significant levels of this effect are evident in boll weevils cells also. Table 1 shows the dose-response endpoints for apoptotic cytopathology in boll weevil and spruce budworm cells. The minimum dose eliciting a 50 percent response is 6 nanograms per ml in spruce budworm cells and 30 nanograms per ml in boll weevil cells.

DNA fragmentation: Spruce budworm, CF124T, cells ($3 \times 10^6$ cells/well) were added to 6-well total volume of 3 ml. The trays were incubated at 28 degrees C. overnight to allow for attachment of cells. The cell monolayers were washed once with unsupplmented medium (TNMFH). One milliliter each of larval derived virus (10 $\mu$g/ml), toxin (CHAPS; 10 $\mu$g/ml), and actinomycin D (4 $\mu$g/ml; positive control) were then added into the respective wells. Boll weevil, BRL-AG-3A, cells were treated as above except that the actinomycin concentration was 1 $\mu$g/ml and viral protein extract was used at 4 $\mu$g/ml and 7.5 $\mu$g/ml. Mock-enfected (sans virus), mock-treated (sans viral extract), and untreated cells were used as negative controls. The treatments were adsorbed for 1 hour at 21 degrees C. on a Bellco rocker platform set at 2.5 rpm. After adsorption, the volume in each well was made up to 3 ml with complete TNMFH (medium containing 10 percent fetal bovine serum and 0.5 $\mu$g/ml gentamicin). Virus-infected cells were incubated for 24 hours at RT and toxin-treated samples were incubated at 28 degrees C. DNA was harvested 24 hours after infection or treatment using 0.4M Tris-HCl pH7.5, 0.1M EDTA, 0.1 percent SDS, and 200 $\mu$g/ml proteinase K solution. After incubation at room temperature for 12–16 hours, samples were phenol extracted, ethanol precipitated, and digested with 20 $\mu$g/ml of RNase A (Sigma) for 30 min. at 37 degrees C. 20 $\mu$g/ml of each sample were then analyzed by agarose gel electrophoresis.

FIG. 5A shows that virus protein extract induces significant host DNA fragmentation at 2.5 $\mu$g/ml in budworm cells. DNA fragmentation is this cell line results in the formation of a ladder effect due to cleavage of cellular DNA into precise lengths. The extent of fragmentation is comparable to that induced by actinomycin D (positive control). Virus-treated cells did not induce any fragmentation with whole virus suggest that establishment of an infection cycle and subsequent expression of a viral apoptosis inhibitor gene might be responsible for the suppression of programmed cell death and ensuing effects. Such inhibitor genes have been detected in viruses.

FIG. 5B shows that DNA fragmentation is induced in boll weevil cells, but to a lesser extent compared to the positive (actinomycin D) control. The mode of DNA fragmentation is cell line dependent; fragmentation in boll weevil cells has always resulted in a smear rather than a ladder effect, due to incremental cleavage of cellular DNA.

The analysis of future expected losses attributable to the boll weevil are based on experiences and trends already evident on the Texas High Plains and are projected 5–10 years into the future. In the furthest north areas where cotton is grown, the damage caused by the boll weevil historically has been light. However, in the High Plains, serious economic damages may be experienced as far north as Floyd, Hale, Lamb, Briscoe and Bailey counties. From these counties and south, annual yield losses of about 15% are projected, along with an increase in insect control cost of $35 to $45 per acre on irrigated cotton and about $20 per acre on dryland cotton. These losses, combined with acreage shifts to alternative crops are reflected in reduced farmer net income from $189 million to $47 million (a loss of $142 million).

Because yield and cost effects of the boll weevil, about 500,000 acres of cotton production is expected to shift to alternative crops, which offers greater profit than cotton under boll weevil pressure. This suggest s a reduction in cotton production of 800,000 bales. The loss of this production would result in the closure of approximately 60 of the current 190 cotton gins in the region.

Compared to other crops, cotton generates relatively more jobs per dollar of production, and has a significantly greater impact on the regional economy. The gross income from acres traditionally planted to cotton is expected to decline from $862 million to $668 million (a loss of $194 million). This will impact the economy of the region by reducing business activity $500 million with a loss of more than 9,000 jobs. The majority of the losses will occur in Floyd, Hale, Lamb, Bailey and Briscoe and counties to the south.

The results based on the most likely estimate of future boll weevil impact indicates that the boll weevil is indeed a serious threat to cotton production and to the economy of the Texas High Plains. Due to uncertainty on exactly how the boll weevil will spread and survive on the Texas High Plains, an upper bound or "worst case" and a lower or "best case" scenario was evaluated to put bounds on the estimates.

Previously we talked about McLaughlin 1972 showing that certain viruses kill boll weevil larvae. We also presented that Cerutti and Devauchelle (1980) taught that viral extract inhibits gene expression/protein synthesis in mosquitos and bud worms. The present invention shows that a protein fraction or extract from purified Chilo iridescent virus partially causes mortality in freshly hatched larvae. A viral extract induces cellular suicide (apoptosis) in boll weevil and bud worm cells. The viral extract inhibits protein synthesis in boll weevil cells. Purified, active protein can be isolated from the viral protein extract and its amino acid sequence can be determined. This information can then be used to isolate and identify the gene for the active polypeptide.

All publications and patents mentioned in this specification are herein incorporated by reference as if each individual publication or patent was specifically and individually stated to be incorporated by reference.

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

What is claimed is:

1. A method of controlling insect pests or insect disease vectors that infest or transmit disease among plants, humans, or animals, comprising applying to the location wherein said insect is to be controlled an insect-controlling amount of a viral protein extract derived from Chilo iridescent virus particles, wherein said viral protein extract is capable of inducing apoptosis in insect cells or inhibiting protein synthesis in insect cells.

2. The method of claim 1 wherein the protein extract is ingested by the insect or introduced to the insect by contact.

3. The method of claim 1 wherein the insect is sprayed with the extract.

4. The method of claim 1 wherein the insect is a member of the order Coleoptera.

5. The method of claim 1 wherein the insect is a boll weevil.

6. The method of claim 1 wherein the insect is freshly hatched beetle larvae.

7. The method of claim 1 wherein the insect is freshly hatched or neonate boll weevil larvae.

8. The method of claim 1 wherein the insect is a household pest or a disease vector.

9. A method for controlling aphids or other members of the order Homoptera on plants by applying an insect-controlling amount of Chilo iridescent virus to the plants.

10. The method of claim 9, wherein the plants are cotton plants.

11. The method of claim 9 wherein the plants are maize, alfalfa, cotton, rape, bean, potato or rice plants.

12. An insect-controlling composition, comprising a suitable carrier and an insect-controlling amount of a viral protein extract derived from Chilo iridescent virus particles, wherein said viral protein extract is capable of inducing apoptosis in insect cells or inhibiting protein synthesis in insect cells.

* * * * *